United States Patent [19]

Shimada et al.

[11] Patent Number: 5,998,384
[45] Date of Patent: Dec. 7, 1999

[54] ENDOSCOPIC ADMINISTRATION OF AN HSV-TK GENE TO TREAT DIGESTIVE ORGAN CANCER

[75] Inventors: Takashi Shimada; Norio Matsukura, both of Tokyo; Osamu Iijima, Ibaraki; Katsuhiko Akiyama, Ibaraki; Takeshi Goto, Ibaraki, all of Japan

[73] Assignee: Hisamitsu Pharmaceutical Co., Inc., Saga, Japan

[21] Appl. No.: 08/949,137

[22] Filed: Oct. 10, 1997

Related U.S. Application Data

[63] Continuation of application No. 08/592,525, Jan. 26, 1996, abandoned.

[51] Int. Cl.$^6$ .............................. A61K 48/00; C12N 5/00; C12N 15/00
[52] U.S. Cl. ..................... 514/44; 424/93.2; 435/320.1; 600/101
[58] Field of Search ............................ 514/44; 424/93.2; 435/320.1, 455; 600/101

[56] References Cited

U.S. PATENT DOCUMENTS

| | | | |
|---|---|---|---|
| 5,631,236 | 5/1997 | Woo et al. | 514/44 |
| 5,641,484 | 6/1997 | Hung et al. | 424/92.3 |
| 5,670,488 | 9/1997 | Gregory et al. | 514/44 |
| 5,786,340 | 7/1998 | Henning et al. | 514/44 |

FOREIGN PATENT DOCUMENTS

| | | |
|---|---|---|
| 6-509328 | 10/1994 | Japan . |
| WO 93/00051 | 1/1993 | WIPO . |

OTHER PUBLICATIONS

Vile et al (1995) Targeted Gene Therapy 9: 190–199.

E. Marshall (1995) Science 269: 1050–1055.

"Significance of Strip Biopsy, with Particular Reference to Endoscopic "Mucosectomy"," Digestive Endoscopy, vol. 1, No. 1 (Oct. 1989), pp. 4–9, Tadayoshi Takemoto et al.

"Laparoscopic Wedge Resection of the Stomach for Early Gastric Cancer Using a Lesion–Lifting Method," Department of Surgery, Keio University School of Medicine, Tokyo, Japan, Masahiro Ohgami et al., Dig Surg 1994; 11:64–67.

"Site–Specific Gene Expression in Vivo by Direct Gene Transfer into the Arterial Wall," Science, vol. 249, Sep. 14, 1990, pp. 1285–1288, Elizabeth G. Nabel et al.

"Gene Therapy for the Treatment of Brain Tumors Using Intra–Tumoral Transduction with the Thymidine Kinase Gene and Intravenous Ganciclovir," Human Gene Therapy 4:39–69 (1993), Edward H. Oldfield, M.D. et al.

"Retroviral Gene Transfer Induced Constitutive Expression of Interleukin–2 or Interferon–γ in Irradiated Human Melanoma Cells," Blood, vol. 80, No. 11 (Dec. 1), 1992: pp. 2817–2825, B. Gansbacher et al.

"Interleukin–2 Production by Tumor Cells Bypasses T Helper Function in the Generation of an Antitumor Response," Cell, vol. 60, pp. 397–403, Feb. 9, 1990, Eric R. Fearon et al.

"Murine Interleukin–4 Displays Potent Anti–Tumor Activity in Vivo," Cell, vol. 57, pp. 503–512, May 5, 1989, Rober I. Tepper et al.

"Exogenous Expression of Mouse Interferon γ cDNA in Mouse Neuroblastoma C1300 Cells Results in Reduced Tumorigenicity by Augmented Anti–Tumor Immunity," Proc. Natl. Acad. Sci. USA vol. 86 pp. 9456–9460, Dec. 1989, Yoshihiko Watanabe et al.

"Vaccination with Irradiated Tumor Cells Engineered to Secrete Murine Granulocyte–Macrophage Colony–Stimulating Factor Stimulates Potent, Specific, and Long–Lasting Anti–Tumor Immunity," Proc. Natl. Acad. Sci. USA vol. 90, pp. 3539–3543, Apr. 1993, Medical Science, Glenn Dranoff et al.

"Murine Tumor Cells Transduced with the Gene For Tumor Necrosis Factor–α", The Journal of Immunology, vol. 146, pp. 3227–3234, No. 9, May 1, 1991, A.L. Asher et al.

"Tumor Rejection After Direct Costimulation of CD8+ T Cells by B7–Transfected Melanoma Cells", Science, vol. 259, Jan. 15, 1993, pp. 368–370, Sarah E. Townsend et al.

"Human Gene Therapy," Science, vol. 256, May 8, 1992, pp. 808–813, W. French Anderson.

"In Vivo Gene Transfer with Retroviral Vector–Producer Cells for Treatment of Experimental Brain Tumors," Science, vol. 256, Jun. 12, 1992, pp. 1550–1553, Kenneth W. Culver et al.

"In Vitro Evidence That Metabolic Cooperation Is Responsible for the Bystander Effect Observed with HSV tk Retroviral Gene Therapy," Human Gene Therapy 4:725–731 (1993), Wan Li Bi et al.

"Suppression of Human Colorectal Carcinoma Cell Growth by Wild–Type p53," Science, vol. 249, pp. 912–915, Suzanne J. Baker et al.

*Primary Examiner*—Deborah Crouch
*Attorney, Agent, or Firm*—Nikaido, Marmelstein Murray & Oram, LLP

[57] ABSTRACT

A therapy for a disease, e.g., gastric cancer, comprising endoscopic local administration of a vector having a gene for treatment or cells producing the vector to a lesion to transduce the gene into target cells. The direct in vivo transduction of a gene for treatment into the affected site is expected to produce therapeutic effects specific on the lesion. Since the gene is introduced also into lymph nodes which may have developed a metastatic lesion, both the primary lesion and the metastatic lesion in the surrounding lymph nodes can be treated simultaneously.

8 Claims, 7 Drawing Sheets

ENDOSCOPIC ADMINISTRATION OF AN HSV-TK GENE TO TREAT DIGESTIVE ORGAN CANCER

This application is a continuation of application Ser. No. 08/592,525, filed Jan. 26, 1996 now abandoned.

FIELD OF THE INVENTION

This invention relates to gene therapy for digestive cancers and the like. More particularly, it relates to a method for transducing a gene for treatment to target cells, such as cancer cells, by endoscopically administering a vector having the gene or cells capable of producing such a vector directly to the affected site, such as a digestive cancer lesion.

BACKGROUND OF THE INVENTION

The rapid progress of genetic engineering has enabled development of various molecular biological techniques. With the development, remarkable advancements have been shown in analyses of genetic information and functions, and a number of attempts to apply the results to actual therapy have been made. Above all, gene therapy is mentioned as one of the fields which received the greatest development. Various genes relating hereditary diseases have been discovered and decoded, while methods for introducing these genes into cells through physical and chemical techniques have been developed. Thus, gene therapy has now stepped up from the stage of fundamental experiments to actual clinical application.

As it has been clarified that the abnormal gene participates in congenital diseases, such as familial hypercholesterolemia and adenosine deaminase (ADA) deficiency, and cancers and AIDS which are considered as acquired hereditary diseases, gene therapy by transducing the gene to the somatic cells of a patient has been attracting attention as a new method of therapy. After the first clinical test of gene therapy in the United States in 1989, clinical tests were commenced also in Italy, The Netherlands, France, England, and China. In the U.S., in particular, 81 protocols for gene therapy were approved by Recombinant DNA Advisory Committee (RAC) of National Institute of Health (NIH), and about 500 cases underwent gene therapy by June, 1995.

By the kind of the cells to which genes are transduced (target cells), gene therapy is divided into germ cell gene therapy and somatic cell gene therapy. It is also divided into augmentation gene therapy (a new (normal) gene is added with an abnormal gene as it is) and replacement gene therapy (an abnormal gene is replaced with a new (normal) gene). For the time being, only augmentation gene therapy to somatic cells are allowed due to bioethical and technical limitations.

A great technical subject in the above-mentioned clinical application of gene therapy is how to introduce foreign genes into target cells efficiently and safely. Early in 1980, application of physical techniques such as microinjection was attempted but not turned to practical use because the efficiency and stability of gene transduction were low and also because the technique of large scale cell culture was limited in those days. Thereafter, recombinant viruses (virus vectors) serving as a vector for efficient transduction of an foreign gene into target cells were developed, which enabled clinical application of gene therapy for the first time.

One of the most general methods of gene therapy is ex vivo gene therapy by autograft, in which target cells are taken from a patient and, after transducing thereto a gene for therapy, the cells are returned to the patient (see Science, Vol. 249, p. 1285 (1990)). Application of ex vivo gene therapy is limited to those cases in which the cells subject to the therapy can be taken outside the body. In addition, since special equipment is required for mass culture of the cells taken from the patient, the facilities available for the therapy are limited.

On the other hand, for the cases where the target cells are fixed at an organ or tissues, so-called in vivo gene therapy has been studied, in which a gene for treatment is administered directly to the site from which the disease is originated. For example, a method for transducing a gene into an organ, such as the heart or the liver, comprising inserting a balloon catheter through a blood vessel and, after stopping the blood flow, directly infusing the gene to the inner wall of the blood vessel has been proposed (see unexamined published Japanese patent application 6-509328 based on a PCT application PCT/US92/05242 (International Publication No. WO93/00051)).

Clinical researches of in vivo gene therapy for cerebroma (see Human Gene Therapy, Vol. 4, p. 39 (1993)) or malignant melanoma (Blood, Vol. 80, p. 2817 (1992)) have also been carried on. Such in vivo gene therapy is expected as a new method taking the place of conventional surgical treatment or chemotherapy.

Gene therapy for cancers is generally divided into indirect killing of cancer cells and direct killing of cancer cells.

The former is a method for treating a cancer by making use of immunity essentially possessed by a living body. More specifically, this method is to make a tumor disappear by enhancing the anti-tumor immunity of the patient by transducing of a gene which codes cytokines, such as interleukin (IL) 2 (see Cell, Vol. 60, p. 397 (1990)), IL 4 (see Cell, Vol. 57, p. 503 (1989)), interferon (INF) γ (see Proc. Natl. Acd. Sci. U.S.A., Vol. 86, p. 9456 (1989)), a granulocyte-macrophage colony-stimulating factor (GM-CSF) (see Proc. Natl. Acd. Sci. U.S.A., Vol. 90, p. 3539 (1993)), and a tumor necrosis factor (TNF) (see J. Immunolo., Vol. 146, p. 3227 (1991)), and an intercellular adhesive factor (see Science, Vol. 259, p. 368 (1993)). With respect to the mechanism of the tumor disappearance, induction of cytotoxic T lymphocytes (CTL) and tumor infiltrating lymphocytes (TIL) has been reported (see Science, Vol. 256, p. 808 (1992)).

The latter therapy is a method of introducing a gene directly acting on cancer cells. Specifically, this method is characterized in that a gene coding an enzyme capable of converting a cytotoxin precursor to an activated form is transduced into cancer cells, and the cytotoxin precursor is administered locally or systemically thereby to specifically kill the transduced cancer cells. The method is called virus-directed enzyme/prodrug therapy (VDEPT). For example, introduction of a self-killing gene, such as a thymidine kinase (tk) gene of herpes simplex virus (HSV), combined with ganciclovir (GCV) is mentioned (see Science, Vol. 256, p. 1550 (1992)). The cells to which the tk gene has been transduced metabolize GCV to produce cytotoxic GCV-triphosphate (GCV-TP) and thereby suffer injury and death. At this time, a lethal effect occurs also in the cancer cells into which the gene has not been integrated (a so-called bystander effect) and the tumor reduces (see Human Gene Therapy, Vol. 4, 725 (1993)). Further, in cases where carcinogenesis is induced by variation of anti-oncogene, such as p53 and Rb, transduction of the anti-oncogene has been suggested in an attempt to normalize the cells (see Science, Vol. 249, p. 912 (1990)).

About a half of cases of gastric cancer, one of digestive organ cancers, are now found in the initial stage owing to the recent highly advanced medical techniques, and more than a half of the cases can be cured completely. However, advanced cases of gastric cancer are still incurable even with every possible treatment, and establishment of new therapy has been keenly demanded.

The conventional treatment for gastric cancer is generally divided into (1) surgical treatment and (2) chemotherapy as described below.

(1) Standard surgical therapy generally applied to gastric cancer is the extended radical surgery comprising complete extirpation of not only the stomach inclusive of the lesion but the surrounding lymph nodes. However, the recent rapid advancement of medical treatment on gastric cancer has allowed application of reduced surgery comprising removal of the affected site to cases with gastric cancer at the early stage with little possibility of spread to lymph nodes. The reduced surgery includes endoscopic mucosal resection, laparoscopic local resection of the stomach, and the like, and the scale of the operation is decided according to the depth of the affected part.

Endoscopic mucosal resection (see Takemoto, T. et al., Digest Endosco., Vol. 1, No. 1, p. 4 (1989)) is a surgical treatment involving no laparotomy. Strip biopsy is widely performed as one embodiment of endoscopic mucosal resection, in which the lesion is lifted by submucous infusion of physiological saline and resected by means of a direct vision 2-channel scope. Strip biopsy is advantageous in that the time for an operation and anesthesia can be reduced and the amount of transfused blood is smaller than that needed in a standard surgical operation so that hepatic disorders can be minimized and the pain or burden on a patient can be alleviated. Although complete extirpation of the surrounding lymph nodes is difficult because the resectable area is limited, an increased capacity of the remaining stomach is secured, making it possible to improve the patient's postoperative quality of life (QOL). However, the cases to which strip biopsy is applicable are limited to those with protuberant tumors having a diameter of smaller than 2 cm and depressed tumors having a diameter of smaller than 1 cm.

For the management of larger lesions which should be removed by divided endoscopic mucosal resection and raise a possibility of increasing an incomplete resection ratio, laparoscopic local stomach resection (see Ohgami, M. et al., Dig. Surg., Vol. 11, pp. 64–67 (1994)) is effective. However, the gas in the stomach may escape through the possible perforation made for the resection. It may follow that the visual field is lost due to deflation of the stomach, which sometimes forces switch-over to laparotomy.

The above-mentioned reduced surgery gives rise to problems of occurrence of multiple cancer and carcinogenesis of the residual stomach and also involves a possibility of metastases. Therefore, care should be taken in resection not to bring the tumor tissue into contact with other tissues. Further, the target of the reduced surgery is a primary cancer that can be surgically resected with ease and accordingly is not expected to have effects on metastatic lesions in lymph nodes.

(2) For the gastric cancer that cannot be completely resected or with observed metastasis to lymph nodes, endoscopic chemotherapy is adopted for the purpose of extirpation of the affected lymph nodes. This method is medication for complete extirpation chiefly aiming at metastatic lesions in lymph nodes that are difficult to extirpate by surgical means. Drugs comprising a lymph-directed carrier, such as an emulsion, liposomes, or fine activated carbon powder, having included therein or adsorbed thereon an anticancer agent are used for the chemotherapy. The anticancer agents include 5-FU, adriamycin, mitomycin C, and so on. However, there is a possibility of occurrence of side effects, such as epilation, reduction of leucocytes, and internal organ disturbances. While it has been proposed to previously transduce a multidrug-resistant gene (MDR-1) into hematopoietic stem cells to endow the patient with resistant against chemotherapy, chemotherapy serves as nothing but preoperative auxiliary treatment for the time being.

Anyway, the above-mentioned therapeutic methods differ in applicability, and there has not been established therapy aiming at a tumor site and surrounding lymph nodes at the same time.

SUMMARY OF THE INVENTION

In the light of the above situation, the inventors have conducted extensive studies for the purpose of providing a method for simultaneously treating a tumor site and a metastatic lesion in a lymph node without relying on a conventional surgical treatment including resection of the tumor site and extirpation of the lymph node. As a result, it has been surprisingly found that when a recombinant virus vector, etc. carrying a gene for treatment is endoscopically delivered directly to a primary lesion, such as a tumor site, by means of a needle, etc., the gene is transduced not only into the primary lesion but specifically to metastatic lesions in lymph nodes and expressed in these sites and thereby expected to produce effects in extirpation of the lymph nodes as well. The present invention has been completed based on this finding.

Accordingly, an object of the present invention is to provide a method for transducing a gene for treatment into the tumor tissue cells of a patient with a digestive cancer or the like by a direct in vivo technique (direct transduction of a gene into an affected site). At the same time, an object of the present invention is to provide a method for transducing a gene for treatment into a metastatic lesion in a lymph node through transfer of a vector for gene therapy to the lymph node, which is a newly found effect. More particularly, the object of the present invention is to provide a method enabling endoscopic treatment of those cases which conventionally require laparotomy for complete extirpation of the subject organ (e.g., stomach) by transducing a gene for treatment also into a metastatic lesion in a lymph node, which has been difficult to treat by conventional endoscopic mucosal resection or laparoscopic local resection of the stomach.

The present invention provides, in its first embodiment, a method for transducing a gene for treatment into an affected site by means of a vector for gene therapy while monitoring the tumor site on a monitor screen.

The present invention also provides, in its second embodiment, a method for not only transducing a gene for treatment into cancer cells by using a virus vector as a gene carrier but also achieving the properties of the virus vector to transfer to lymph nodes by the above-mentioned endoscopic topical administration.

From the above viewpoint, the present invention further provides, in its third embodiment, a method for transducing a gene for treatment into lymph nodes surrounding a tumor site by making use of the virus vector's properties of transferring to the lymph nodes, which comprises topically injecting the virus vector into the submucous layer surrounding a tumor by the above-described method.

The present invention furthermore provides, in its fourth embodiment, a specific therapeutic method which makes use of a thymidine kinase gene of human herpes simplex virus origin which has been transduced into a primary cancer lesion and a metastatic lesion by means of a virus vector.

According to the first embodiment, a carrier for a gene for treatment, such as a virus vector, can be topically injected to an affected site while observing through a monitor. As a result, a gene included in the carrier, e.g., a virus vector, can be transduced specifically into cancer cells.

According to the second embodiment, a gene for treatment is transduced into tumor cells by means of a carrier, such as a virus vector, which carries the gene and has been topically injected under endoscopic observation. In addition, the carrier is given properties of transferring to lymph nodes and is directed to and accumulated in the lymph nodes.

According to the third and forth embodiments, a gene for treatment can be transduced into lymph nodes by means of a carrier for the gene for treatment, such as a virus vector. Therefore, the metastatic lesions in the lymph nodes can be cured without extirpating the lymph nodes, thereby to prevent recurrence of the cancer.

BRIEF DESCRIPTION OF THE DRAWINGS

The file of this patent contains at least one drawing executed in color. Copies of this patent with color drawing (s) will be provided by the Patent and Trademark Office upon request and payment of the necessary fee.

DETAILED DESCRIPTION OF THE INVENTION

Figure 1:
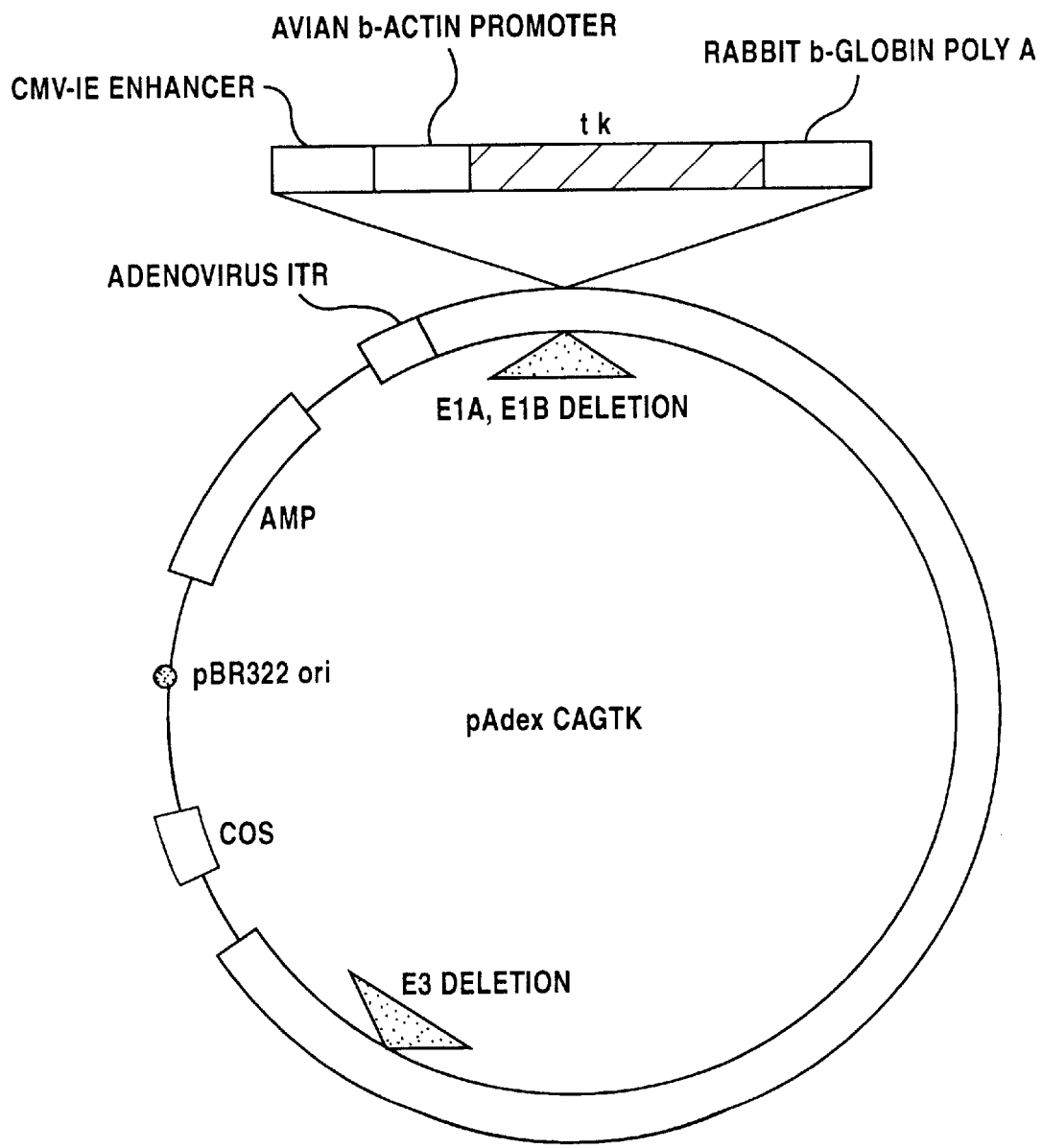
FIG. 1 is a schematic illustration showing the structure of an expression cosmid pAdexCAGTK having a tk-coding gene inserted.

The subjects of the therapy according to the present invention are, for example, vertebrates, preferably warm-blooded animals, still preferably mammals, and particularly preferably humans.

The therapy of the present invention is applicable to all the diseases that can be treated with an endoscope. Examples of such diseases include digestive organ cancers, such as gastric cancer and colon and rectum cancer, pulmonary cancer, urinary bladder cancer, and mammary cancer, especially gastric cancer.

The gene for treatment which can be used in the gene therapy of the present invention is not limited to self-killing genes such as a tk gene and includes any kind of genes which can be used for treatment of disease, in particular, those suppress growth or metastasis of cancer cells. Examples of usable genes for treatment include tumor suppressor genes, such as p53 (see Baker, S. J. et al., *Science*, Vol. 249, p. 912 (1990)), Rb (see Bookstein R. et al., *Science*, Vol. 247, p. 712 (1987)), and WT-1 (see Weissman, B. E. et al., *Science*, Vol. 236, p. 175 (1987); and metastasis suppressor genes, such as TIMP (see Tsuchiya, Y. et al., *Cancer Res.*, Vol. 53, p. 1397 (1993)).

These genes for treatment are usually used after integrating it into a carrier that can express the gene (e.g., a vector) by general genetic recombination techniques. Such a vector includes those of virus origin, such as an adenovirus vector (hereinafter described in Examples), a retrovirus vector (see Miller, A. D., *Current Topics in Microbiology and Immunology*, Vol. 158, p. 1 (1992), etc.), a herpes virus vector (see Palella T. D., *Mol. Cell Biol.*, Vol. 8, p. 457 (1988), etc.), HIV, and an adeno-associated virus vector (see Muzyczka, N., *Current Topics in Microbiology and Immunology*, Vol. 158, p. 97 (1992), etc. Any other virus vectors and non-virus vectors, such as liposomes and polyamino acids, which can carry a gene for treatment can be used. In addition, cells capable of producing a virus vector can be used to provide a virus vector for gene therapy. In such a case, cells capable of producing a virus vector may preferably be suspended as complete as possible in order to avoid clogginess of the syringe for injection.

The vector having integrated therein a gene for treatment is given through, for example, a needle, and is therefore preferably administered as dissolved in a solvent. The solvent to be used is not limited as long as the vector, when suspended therein, does not undergo reduction in titre. Physiological saline, an isotonic phosphate buffer or an isotonic glucose solution is preferred as solvent. In order to improve storage stability of the vector, a stabilizer, e.g., gelatin, may be added to the vector solution. In order to prevent leakage of the vector injected to the affected site, a thickener may be added to the vector solution.

The titre of the vector for gene therapy is preferably $1 \times 10^7$ cfu/ml, more preferably $1 \times 10^8$ cfu/ml, since effective effect of treatment is expected by the increased gene transduction efficiency. The amount of the solution or suspension containing the vector for gene therapy to be administered is preferably from 0.01 ml to 30 ml, and more preferably 0.1 ml to 10 ml.

The endoscope which can be used in the present invention is not particularly limited as long as a needle for injecting a virus vector or virus vector-producing cells can be fitted thereto.

Nucleotide analogues which can be administered after injection of a virus vector into a lesion is preferably ganciclovir (hereinafter abbreviated as GCV). The nucleotide analogue, e.g., GCV, is usually administered intravenously, preferably by an intravenous drip over 1 hour of about 6 mg/kg per day.

The present invention will now be illustrated in greater detail by way of Examples with reference to the accompanying drawings, but it should be understood that the present invention is not construed as being limited thereto.

EXAMPLE 1

Figure 2:
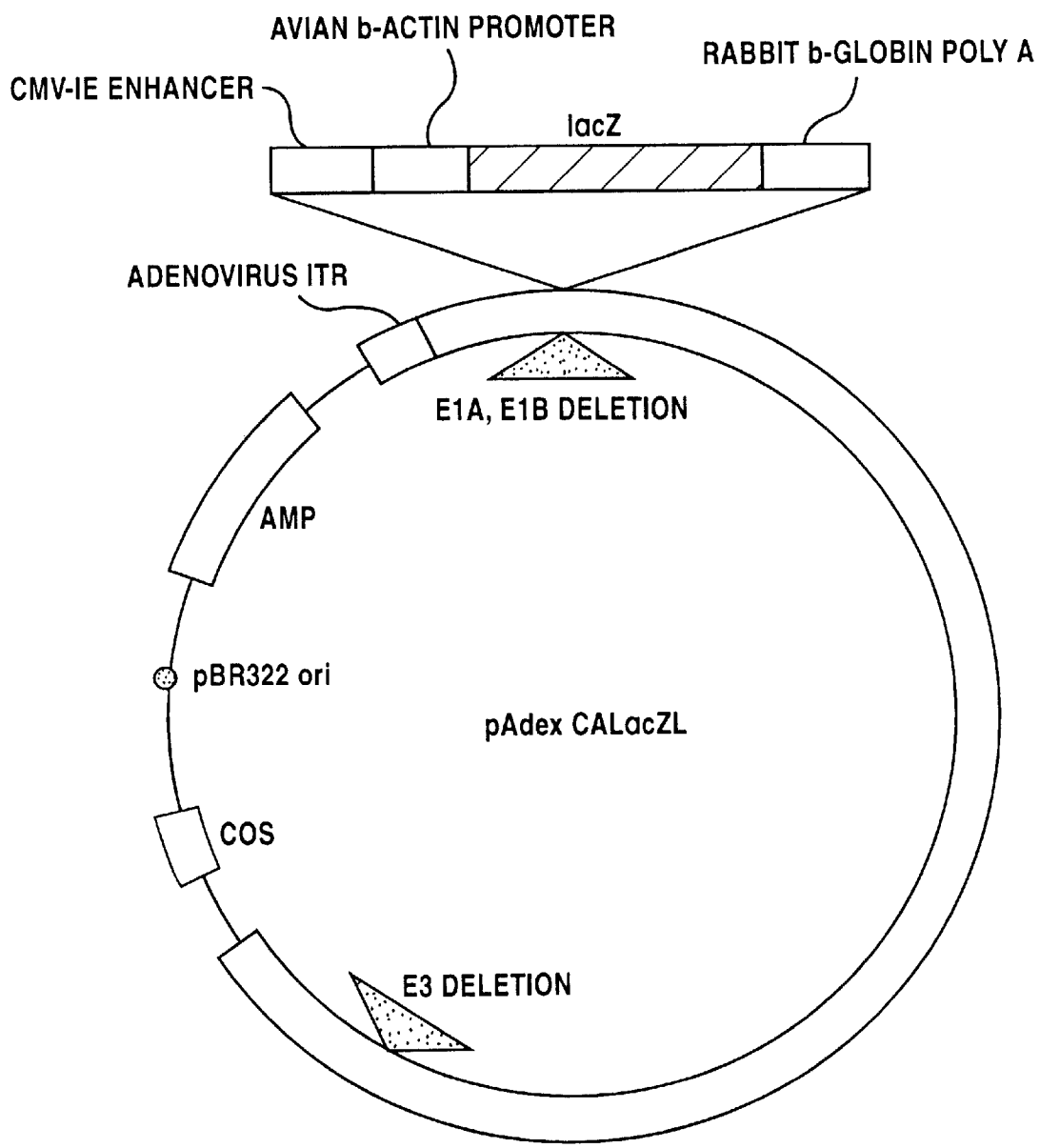
FIG. 2 is a schematic illustration showing the structure of an expression cosmid pAdexCALacZL having a lacZ-coding gene inserted.

Preparation of Recombinant Adenovirus Vector Having tk Gene of Human Herpes Simplex Virus Origin A recombinant adenovirus vector to be used for tk gene expression (FIG. 1) and a recombinant adenovirus vector having a lacZ gene (FIG. 2) were prepared by a COS-TPC method in a known manner (see Kanegae, Y. et al., *Jikken*

*Kagaku,* Vol. 12, No. 3 (1994) and Kanegae, Y. et al., *Jpn. J. Med. Sci. Biol.*, Vol. 47, p. 157 (1994)). All the manipulations concerning the construction of plasmids were in accordance with general gene recombination techniques.

EXAMPLE 2
Preparation of Gastric Cancer Model in Beagle

A 4-month-old male beagle was allowed drink water containing 5 mg/500 ml of N-ethyl-N'-nitro-N-nitrosoguanidine (ENNG) every day for a 8-month period and then fed under usual conditions for 6 months to develop a tumor.

EXAMPLE 3
Confirmation of Tumor with Endoscope

An endoscope EVIS 200 System manufactured by Olympus Optical Co., Ltd. was used.

The beagle was deprived of food from the previous day of endoscopic observation. Anesthesia was induced by intramuscular injection of 10 mg of Ketalar (produced by Sankyo Co., Ltd.) and maintained by inhalation of 2% Halothane (produced by Hoechst A. G.) by means of an automatic respiratory apparatus at an oxygen-nitrous oxide ratio of 1:3. An endotracheal tube with a cuff was inserted into the respiratory tract by using a mouth gag (Termo Corp.) to secure air passage, followed by mechanical aeration. The endoscope was inserted along the upper part of the larynx to confirm the tumor on the monitor screen. Further, the tumor tissue was collected by means of a clamp (produced by Olympus Optical Co., Ltd.), and the tissue was subjected to pathological examination to confirm carcinogenesis of the cells.

EXAMPLE 4
Administration of Virus Vector under Endoscopic Observation

A needle for esophageal varix puncture (produced by Sumitomo Bakelite Co., Ltd.) was inserted into the stomach through the endoscope and the recombinant adenovirus vector ($5 \times 10^8$ cells/500 μl) was directly infused to the tumor site while observing on the monitor screen. After the infusion, the needle was not removed for about 1 minute so that the vector solution might not leak from the mucous membrane and might thoroughly penetrate the tumor site. The vector may be injected by a means other than the above-described needle, for example, a branched catheter with a needle for injection being fitted to each of the tips of the branches.

EXAMPLE 5
Confirmation of Gene-transduced Site by Marker

Figure 3:
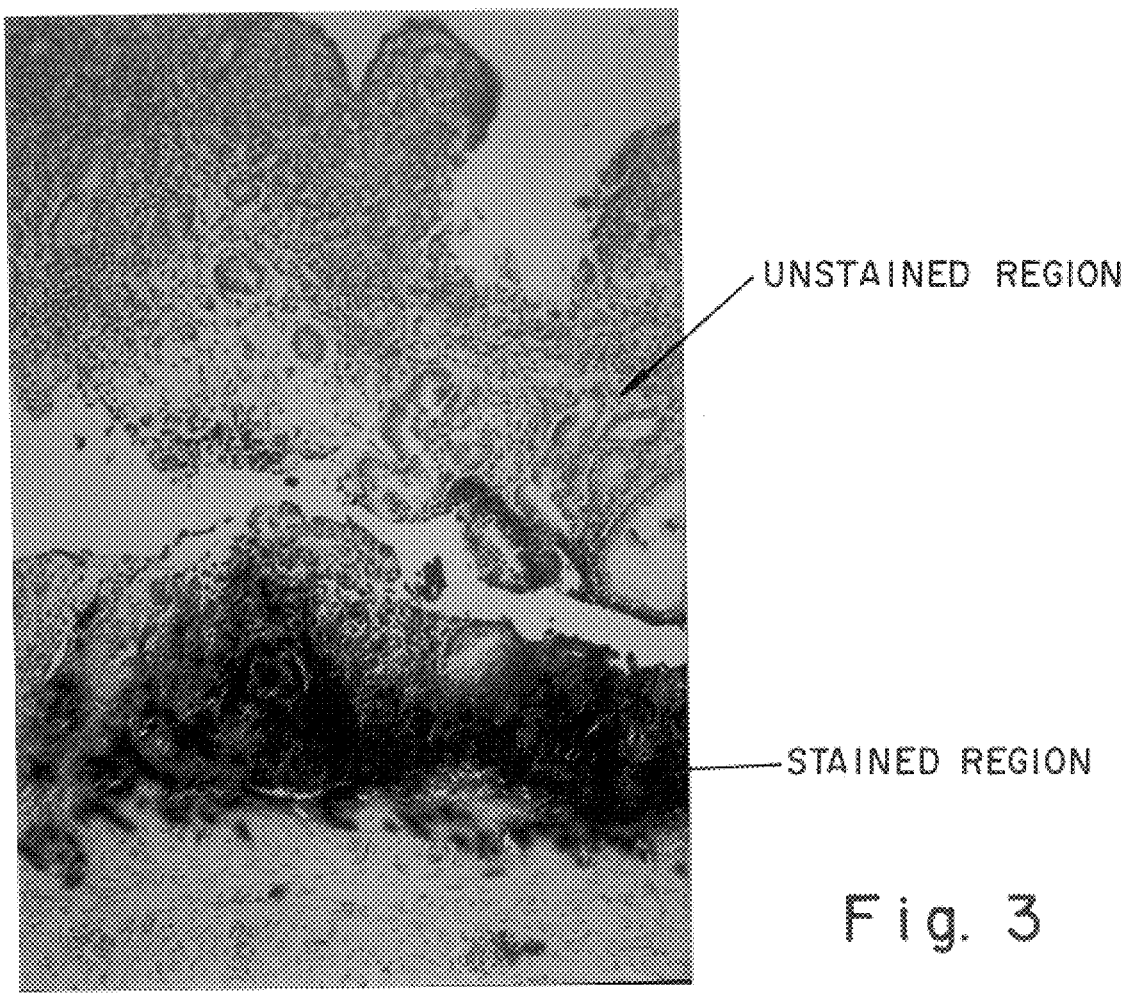
FIG. 3 is an electron micrograph of the X-gal-stained gastric mucous layer preparation to which a gene for treatment has been transduced.
Figure 4:
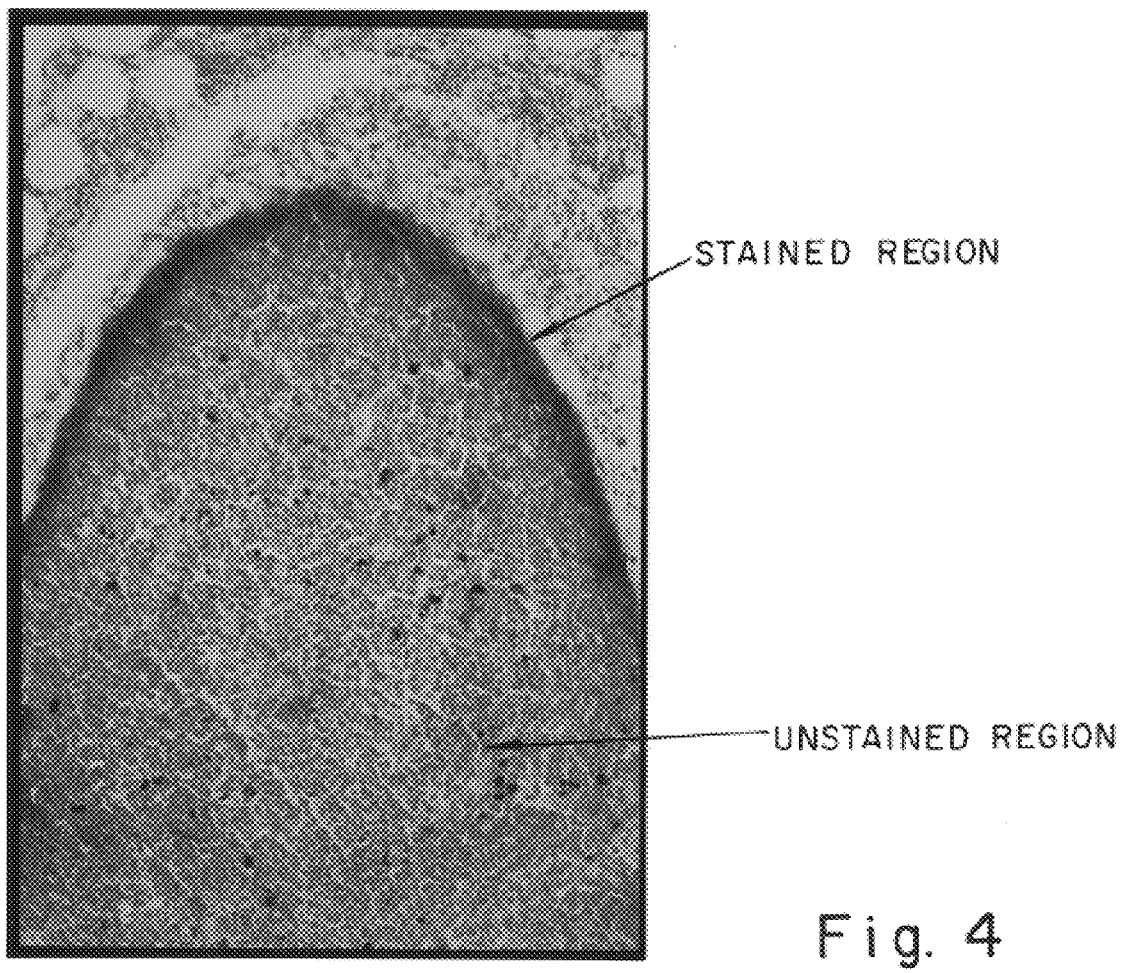
FIG. 4 is an electron micrograph of the X-gal-stained lymph node preparation to which a gene for treatment has been transduced.

A recombinant adenovirus vector having a lacZ gene prepared in Example 1 was locally injected to the submucous layer at the gastric tumor site of the beagle, and the dog was fed in a usual manner for 3 days and subjected to an autopsy. The stomach was excised, cut into pieces, and stained with a staining solution containing X-gal as a substrate. Microscopic observation of a cut piece at an appropriate magnification revealed a plurality of blue-stained areas, confirming to the transduction of the gene into the tumor submucous layer (FIG. 3). In contrast, there was observed no blue-stained area in the control area distant from the injected area. In the autopsy, the surrounding lymph nodes and other tissues were also excised and stained similarly. As a result, the lymph nodes were also found stained, confirming to the transduction of the gene into the lymph nodes (FIG. 4).

EXAMPLE 6
Therapy of Tumor Tissue by GCV Administration

Figure 5:
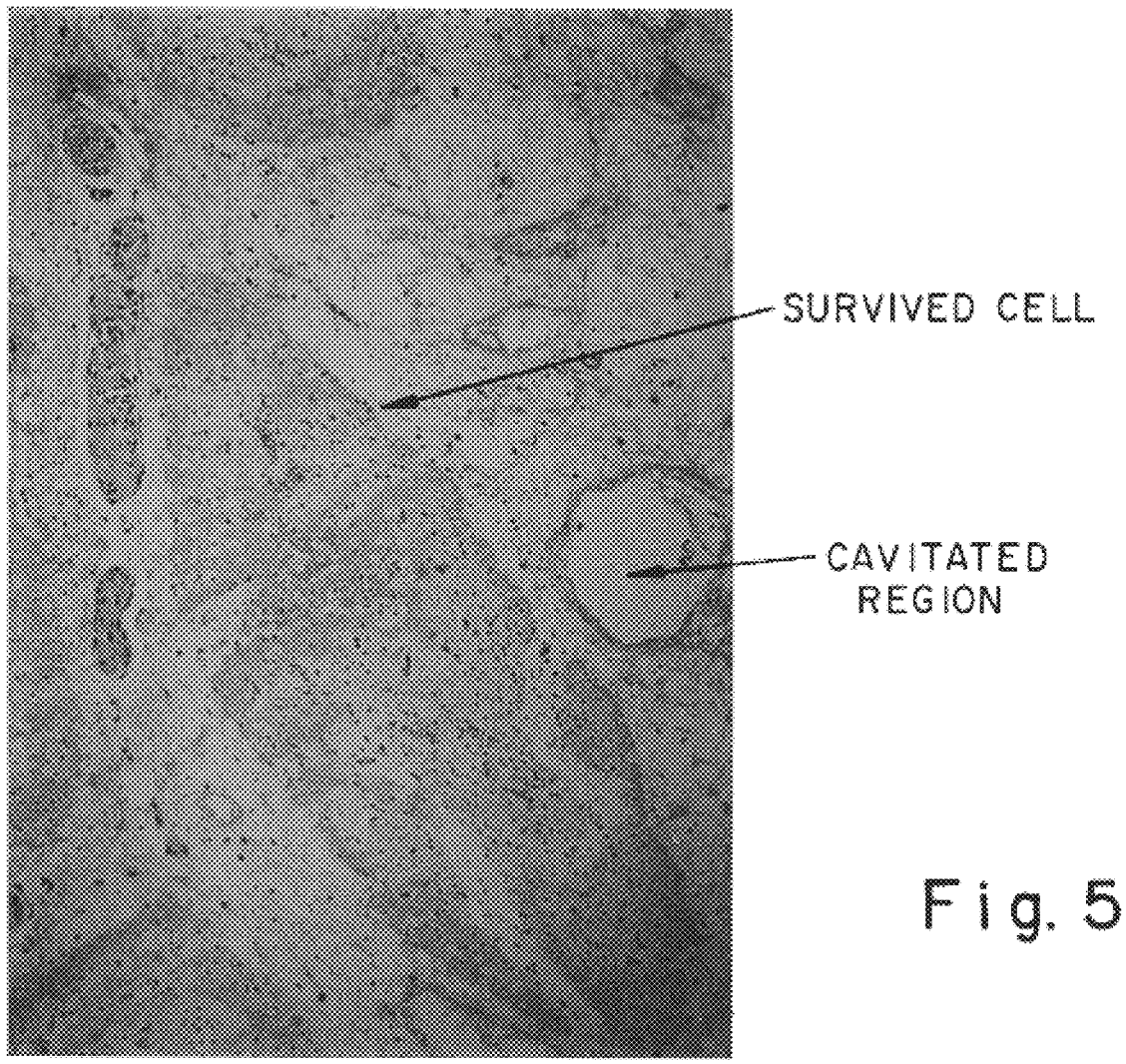
FIG. 5 is an electron micrograph of the gastric mucous layer preparation which shows reduction of tissues as a result of GCV administration.
Figure 6:
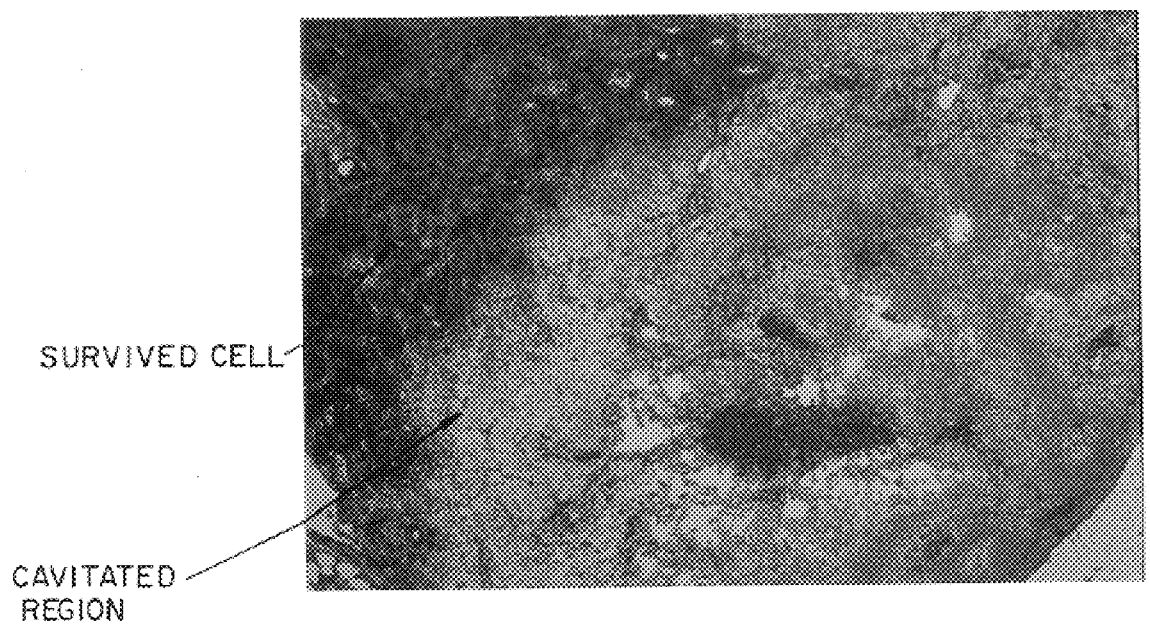
FIG. 6 is an electron micrograph of the lymph node preparation which shows reduction of tissues as a result of ganciclovir administration.
Figure 7:
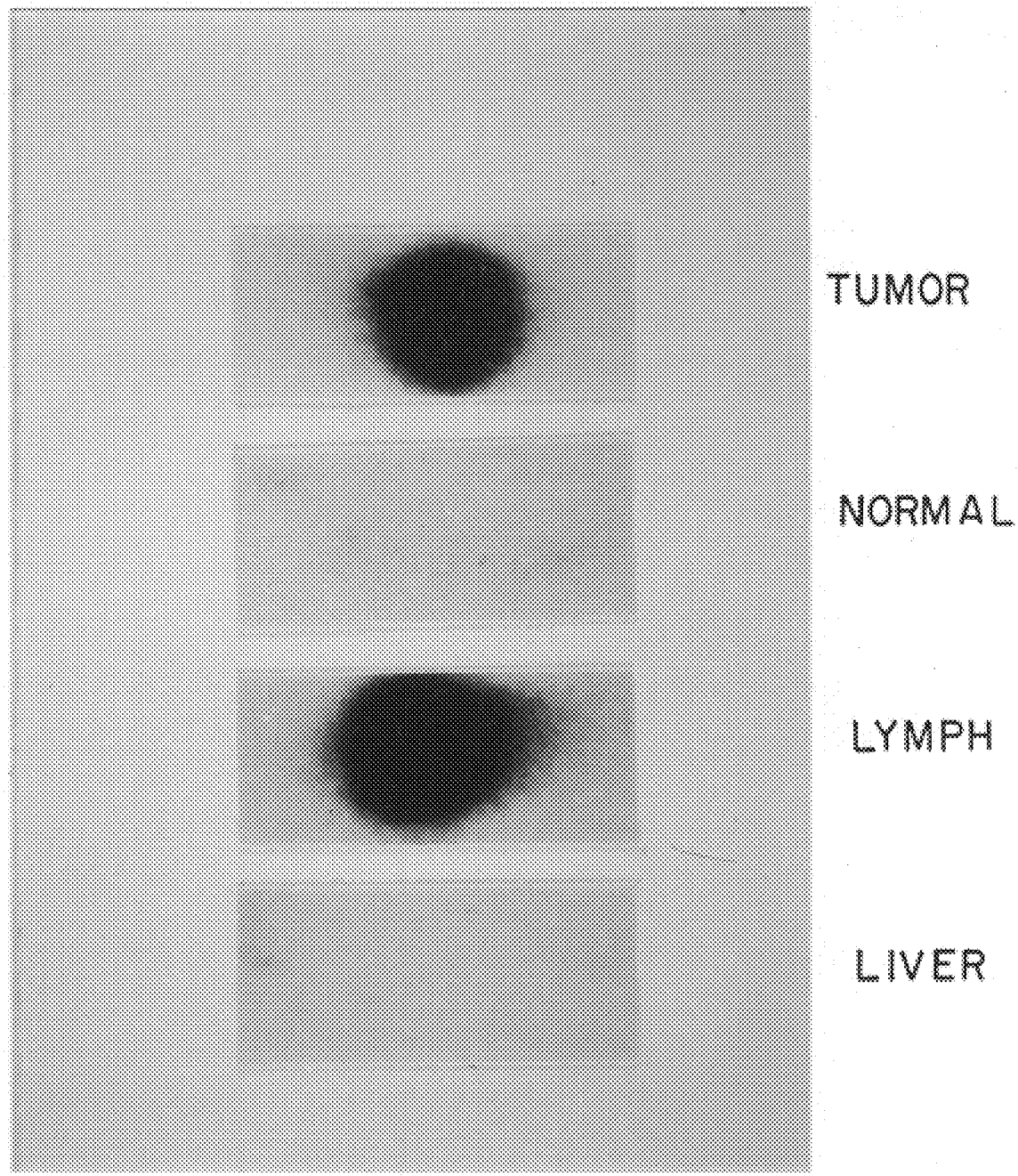
FIG. 7 shows the results of Southern hybridization of the whole DNA prepared from the transduced gastric mucosa and lymph node, with a tk gene as a probe.

The recombinant adenovirus vector with a tk gene prepared in Example 1 was locally injected to the gastric cancer submucous layer according to the above-described method. From the next day, 50 mg/kg of GCV was intravenously injected twice a day (morning and evening) in a total daily dose of 100 mg/kg, and the dog was fed for 4 days, followed by an autopsy to conduct histological study. The cells into which the tk gene was transduced suffered cell injury and finally death due to specific metabolism of GCV. As a result, the histological study revealed cavity formation in the tissues surrounding the tumor site (FIG. 5) and in the lymph nodes (FIG. 6). The whole DNA at the tumor site was prepared and subjected to Southern hybridization with a tk gene as a probe. As a result, it was confirmed that the aimed gene had been transduced specifically into the tumor and the surrounding lymph nodes (FIG. 7).

As described in detail, the therapy according to the present invention enables in vivo transduction of a gene for treatment directly into the target site, which makes specific treatment of only the affected site possible. Further, the gene for treatment can also be introduced to the surrounding lymph nodes. Accordingly, the present invention offers gene therapy showing remarkable effects on both the primary cancer lesions and metastatic lesions in the lymph nodes.

While the invention has been described in detail and with reference to specific embodiments thereof, it will be apparent to one skilled in the art that various changes and modifications can be made therein without departing from the spirit and scope thereof.

What is claimed is:

1. A method for the treatment of a cancer of a digestive organ and a cancer which has metastasized from the cancer of the digestive organ to lymph nodes proximate said cancer of the digestive organ, comprising the steps of locally administering an adenovirus vector containing a herpes simplex virus thymidine kinase gene operatively linked to a promoter or cells producing said adenovirus vector to said cancer of the digestive organ under observation with an endoscope, transducing said gene into target digestive cancer cells and cancer cells metastasized to said lymph nodes and expressing said transduced gene, and thereafter exposing said target digestive cancer cells and said cancer cells metastasized to said lymph nodes to a cytotoxic compound by administering a nucleotide analogue as a substrate for thymidine kinase and converting said nucleotide analogue to said cytotoxic compound with thymidine kinase, wherein production of said cytotoxic compound results in injuring or killing said target digestive cancer cells and said cancer cells metastasized to said lymph nodes.

2. The method according to claim 1, wherein said cancer is gastric cancer.

3. The method according to claim 1, wherein said thymidine kinase gene is human herpes simplex virus thymidine kinase gene.

4. The method according to claim 3, wherein said cancer is gastric cancer.

5. The method according to claim 3, wherein said nucleotide analogue is ganciclovir.

6. The method according to claim 1, wherein said nucleotide analogue is ganciclovir.

7. The method of claim 1, wherein said treatment reduces the sizes of said cancer of the digestive organ and said cancer which has metastasized to said lymph nodes.

8. A method for injuring or killing cells of a gastric cancer and cancer cells which have metastasized from the gastric cancer to lymph nodes proximate the gastric cancer, comprising the steps of locally administering an adenovirus vector containing a herpes simplex virus thymidine kinase gene operatively linked to a promoter or cells producing said adenovirus vector to said gastric cancer under observation with an endoscope, transducing said gene into said cells of the gastric cancer and said cancer cells metastasized to said lymph nodes, and expressing said transduced gene, and thereafter exposing said cells of the gastric cancer and said cancer cells metastasized to said lymph nodes to a cytotoxic compound by administering ganciclovir as a substrate for thymidine kinase, and converting said ganciclovir to said cytotoxic compound by thymidine kinase, wherein production of said cytotoxic compound results in injuring or killing said cells of the gastric cancer and said cancer cells metastasized to said lymph nodes.

* * * * *